United States Patent [19]

Takahashi et al.

[11] Patent Number: 4,829,026
[45] Date of Patent: May 9, 1989

[54] GLASS CERAMICS

[75] Inventors: Katsuaki Takahashi, Okayama; Yoshinari Miura, Hyogo; Akiyoshi Osaka, Okayama; Masayuki Asada, Kurashiki, all of Japan

[73] Assignee: Kuraray Co., Ltd., Kurashiki City, Japan

[21] Appl. No.: 191,177

[22] Filed: May 6, 1988

[51] Int. Cl.$^4$ ............................................. C03C 10/02
[52] U.S. Cl. ..................................................... 501/10
[58] Field of Search ..................................... 501/10, 47

[56] References Cited

U.S. PATENT DOCUMENTS 3,981,736  9/1976  Broemer et al. ................... 501/10
4,617,279 10/1986  Manabe et al. ................... 501/10
4,652,534  3/1987  Kasaga ............................. 501/10
4,698,318 10/1987  Vogel et al. ...................... 501/10

FOREIGN PATENT DOCUMENTS 63-021237  1/1988  Japan .

Primary Examiner—Mark L. Bell
Attorney, Agent, or Firm—Burns, Doane, Swecker & Mathis

[57] ABSTRACT

A glass ceramic comprising at least 90 weight percent of a glass composed of
  CaO : 17–28 weight percent
  $P_2O_5$ : 13–26 weight percent
  $Al_2O_3$ : 25–38 weight percent
  $B_2O_3$ : 20–37 weight percent (all based on the total weight of the glass ceramic),
with the atomic ratio of calcium to phosphorus within the range of 1.30 to 1.75, and apatite crystals dispersed as dominant crystals in said glass.

This glass ceramic is particularly useful as a biological material.

2 Claims, 1 Drawing Sheet

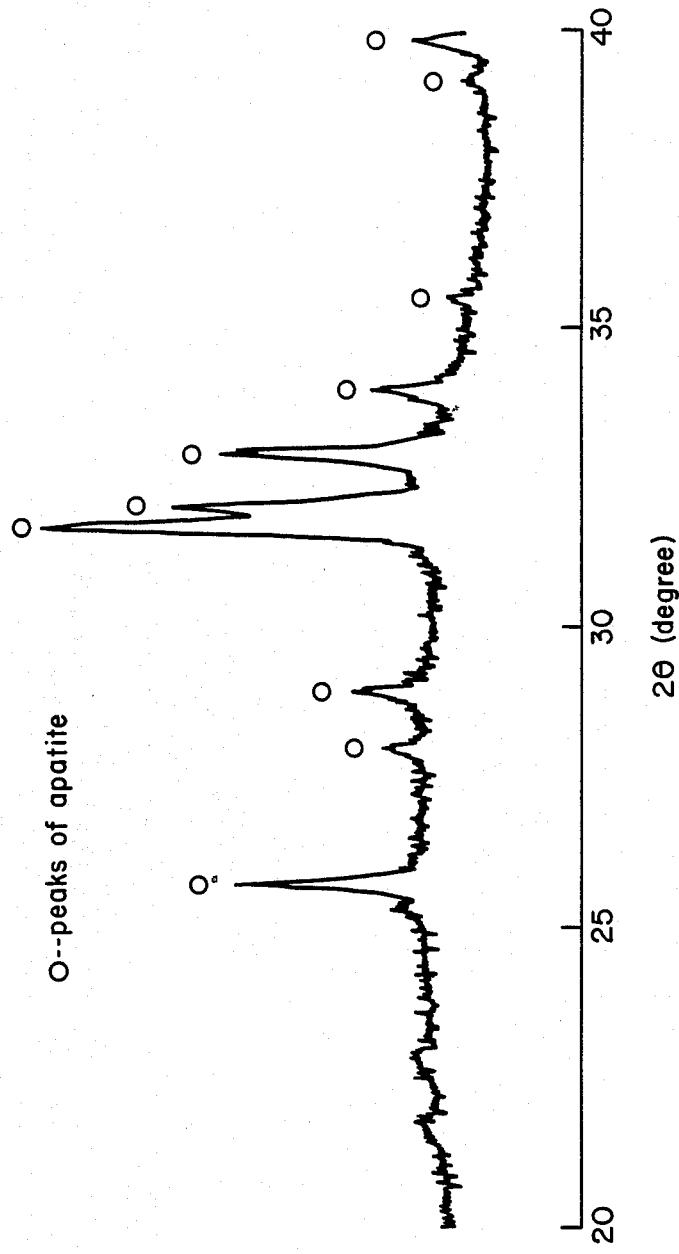

GLASS CERAMICS

BACKGROUND OF THE INVENTION

1. Field of the Invention

The present invention relates to glass ceramics and, more particularly, to a glass ceramic for use in biological applications such as prostheses including artificial crowns, artificial dental roots and artificial bones.

2. Brief Description of the Prior Art

Several different glass ceramics each containing calcium phosphate crystals for use as biological materials have heretofore been reported. These glass ceramics can be roughly classified into the following three types. The first type is based on CaO and $P_2O_5$ and contains $CaO.P_2O_5$ as a crystal phase as described in Japanese Unexamined Patent Application No. 73019/1976. The second type is based on MgO, $SiO_2$, CaO and $P_2O_5$ and contains apatite crystals and crystals of silicates such as wollastonite, diopside, mica, etc. as crystal phases as described in Japanese Unexamined Patent Application No. 191252/1982. The third type is based on CaO, $P_2O_5$, $SiO_2$, $Al_2O_3$ and $B_2O_3$ and contains tricalcium phosphate as a dominant crystal phase as described in Japanese Unexamined Patent Application No. 26743/1981.

The advantage of using a glass ceramic as a biological material is that the glass ceramic is highly biocompatible due to the presence of calcium phosphate crystals in it. Another advantage is, being a type of glass, it can be cast from a melt and, then, crystallized to directly give a product having a desired shape with high dimensional accuracy. However, in regard to the first mentioned type of glass ceramic based on CaO and $P_2O_5$, it is well known that a stable glass is available only in the region of not more than 56 mole percent of CaO, that is to say in the Ca/P range of <0.64. [Sumio Sakka et al (ed.): Glass Handbook, Asakura Shoten, p. 882 (1975)]. For this reason, the product glass ceramic is inadequate in water resistance and hence tends to release its components in vivo to lower the pH of the local humor to manifest an adverse effect on the living body.

Improvements in water resistance may be achieved by increasing the Ca/P ratio of glass but because of the above-mentioned glass-forming region, it is actually difficult to obtain a glass ceramic having a sufficiently high water resistance unless other glass network former such as $SiO_2$ and $B_2O_3$ are present together with the phosphate component.

Glass ceramics of the above-mentioned second and third types are the products developed to meet the above requirement. However, the fusing temperature of the second type of glass is as high as 1,400°–1,500° C. and can hardly been cast with the conventional technologies applicable to the metals. Because the silicate crystal has a strong tendency of inducing surface devitrification, it is very difficult to directly crystallize pre-cast glass bodies having this type of composition. Therefore, it is necessary to pulverize the glass, shape the glass powder into a desirable article by pressing or conventional method for ceramics and, then sinter to crystallize the green body by post-heating. This entails difficulties in regard to the maintenance of dimensional accuracy.

The third type of glass can be fused at a somewhat lower temperature than the second type of glass but its drawback is that a majority of precipitated crystals are tricalcium phosphate crystals with a Ca/P ratio of 1.5. However, in order to overcome the above-mentioned problem of in vivo release of glass components, it is desirable that apatite crystals with a higher Ca/P ratio than 1.5 is precipitated.

SUMMARY OF THE INVENTION

It is an object of the present invention to provide a novel glass ceramic which is highly biocompatible, fusible at a comparatively low temperature and crystallizable as a cast product.

It is a further object of the invention to provide a glass ceramic which is highly suitable for use as a biological material such as various prostheses.

BRIEF DESCRIPTION OF THE DRAWING

FIG. 1 is an X-ray diffraction pattern of a glass ceramic obtained in Example 2 of this invention.

DETAILED DESCRIPTION OF THE PREFERRED EMBODIMENT

The above-mentioned object has been accomplished by the present invention which is directed to:

a glass ceramic comprising at least 90 weight percent of a glass composed of 17 to 28 weight percent of CaO, 13 to 26 weight percent of $P_2O_5$, 25 to 38 weight percent of $Al_2O_3$ and 20 to 37 weight percent of $B_2O_3$, with an atomic ratio of Ca to P within the range of 1.30 to 1.75, and with apatite crystals dispersed as a dominant crystal phase in said glass. The glass ceramic may optionally contain not more than 10 weight percent of additives such as a nucleating agent which will be described hereinafter. The glass ceramic of the invention can be manufactured by melting raw powders of the above-mentioned composition, solidifying the melt and heat-treating the resulting solid body at a temperature not less than the crystallization temperature of apatite to cause a precipitation of apatite crystals dispersed in the glass matrix. The total proportion of the aforementioned quaternary composition of CaO, $P_2O_5$, $Al_2O_3$ and $B_2O_3$ in the glass ceramic is at least 90 weight percent. If the proportion is less than 90 weight percent, uncontrollable crystallization takes place on solidification of the glass melt to frustrate the production of a cast product composed exclusively of glass phase and/or the amount of precipitated crystals by heat-treatment is decreased. The glass ceramic according to the present invention is further characterized in that the atomic ratio of Ca to P is within the range of 1.30 to 1.75. If the Ca/P ratio is less than 1.30, the precipitated crystal phase will become mostly composed of non-apatite phosphate crystals, while no homogenous glass ceramic can be obtained when the Ca/P ratio exceeds 1.75. Furthermore, when the proportion of CaO in the quaternary glass composition is less than 17 weight percent, there will be no precipitation of apatite crystals. Conversely when the proportion of CaO exceeds 28 weight percent, the glass tends to become markedly devitrified so that a cast product composed solely of glass phase cannot be obtained. Referring, further, to the above-mentioned quaternary matrix composition, if the proportion of $P_2O_5$ is less than 13 weight percent, there will be no precipitation of crystals or only a small amount of precipitation, while the presence of $P_2O_5$ in excess of 26 weight percent results in a predominant precipitation of non-apatite phosphate crystals.

As regards the proportion of $Al_2O_3$, if it is less than 25 weight percent, there cannot be obtained a cast product composed exclusively of glass phase, while the presence of $Al_2O_3$ in excess of 38 weight percent causes the difficulty of melting the glass batch (composition). The proportion of $B_2O_3$ should be in the range of 20 to 37 weight percent as mentioned above. If the proportion of $B_2O_3$ is less than 20 weight percent, there cannot be obtained a cast product composed exclusively of glass phase, while the presence of $B_2O_3$ in excess of 37 weight percent results in a marked decrease in the amount of precipitation of crystals. For the reasons mentioned above, the quaternary matrix composition should be as defined hereinbefore and is preferably within the following range: 21 to 28 weight percent of CaO, 15 to 26 weight percent of $P_2O_5$, 25 to 38 weight percent of $Al_2O_3$ and 20 to 37 weight percent of $B_2O_3$, with an atomic ratio of Ca to P within the range of 1.50 to 1.70.

In addition to the above quaternary matrix composition, the glass ceramic of the invention may contain up to 10 weight percent of one or more nucleating and/or other additives such as $Li_2O$, $Na_2O$, $K_2O$, $MgO$, $SrO$, $BaO$, $Y_2O_3$, $La_2O_3$, $TiO_2$, $ZrO_2$, $Nb_2O_5$, $Ta_2O_5$, $CaF_2$, $MgF_2$, $SiO_2$, Au, Pt, Ag, Pd, Rh. The total level of these additives should be less than 10 weight percent, for if this level is exceeded, there will not be obtained a homogeneous glass ceramic, or the amount of precipitation of crystals is decreased.

In the glass ceramic of this invention, apatite crystals occur as dominant crystals dispersed in the glass matrix, although tricalcium phosphate crystals, aluminum phosphate crystals, etc. may also be present as concomitantly dispersed. The term "dominant crystals of apatite" as used in this specification means that the main peak intensity of apatite is greater than those of any other crystals in the X-ray diffraction pattern of the resulting glass ceramic. The apatite used in this invention includes hydroxyapatite $Ca_{10}(PO_4)_6(OH)_2$, and those apatites in which a hydroxyl group(s) is substituted with oxygen or fluorine and show similar x-ray diffraction patterns.

The glass ceramic of the present invention can be manufactured by the following and other processes.

The raw materials are weighed in proportions to assure the defined composition, and ground or milled together. The mixed powder thus obtained is melted in a glass-melting furnace or crucible at 1,200° to 1,400° C. in the usual manner. As the raw glass materials, the oxide, hydroxide, carbonate, nitrate, of each constituent can be utilized and, as calcium and phosphate materials, various calcium phosphates can also be employed. Thus, types of raw materials are optional only if the glass melt shows the defined composition. In melting the material powder, it is preferably to use a crucible which is resistant to corrosion by molten glass but any other appropriate melting furnace can be employed. The glass melt is then cast in a mold or, if necessary, subjected to compression or centrifugal casting to give a cast product having a desired shape.

The cast product is then placed in an electric furnace and heat-treated to be crystallized. The heating is such that the furnace temperature is first increased progressively from room temperature at a rate not exceeding 400° C./hour to 600°–900° C., at which level the temperature is kept for a suitable time, followed by gradual reduction in temperature to room temperature generally at a rate not exceeding 400° C./hour. The above holding time is selected according to the relation between the composition of glass and the crystallization temperature. The crystallization temperature is chosen in view of the exothermic peak in differential thermal analysis of the cast product. As aforesaid, the precipitated crystal phases can be easily identified by X-ray diffraction analysis. The glass produced by the above process is a colorless transparent block which, on crystallization treatment, gives a glass ceramic of the invention in which apatite crystals have been precipitated as dominant crystals in the matrix. The following examples are further illustrative of the invention and should by no means be construed as delimiting its scope.

EXAMPLE 1

$CaCO_3$, $NH_4H_2PO_4$, $Al(OH)_3$ and $B_2O_3$ were taken in necessary proportions to give a glass composition of 25.1 wt. % of CaO, 24.7 wt. % of $P_2O_5$, 29.8 wt. % of $Al_2O_3$ and 20.4 wt. % of $B_2O_3$ (Ca/P=1.67) and ground in a mortar. This glass batch was melted in an alumina cricible at 1,350° C. for 3 hours and poured into a mold to give a rectangular block measuring $10 \times 10 \times 20$ mm$^3$. this glass block was then heat-treated at 800° C. for 50 hours, whereby fine crystals were precipitated. X-ray diffraction analysis showed that these crystals were apatite, tricalcium phosphate and aluminum phosphate crystals, with the peak intensity of apatite crystals being the greatest of all.

EXAMPLE 2

A glass batch of the same composition as that used in Example 1 was maintained at 750° C. for 50 hours. As a result, fine crystals were precipitated as in Example 1. by X-ray diffraction analysis, these crystals were confirmed to be apatite crystals.

EXAMPLE 3

$CaCO_3$, $H_3PO_4$, $Al_2O_3$ and $B_2O_3$ were taken to give a glass composition of 21.1 wt. % of CaO, 15.9 wt. % of $P_2O_5$ 37.4 wt. % of $Al_2O_3$ and 25.6 wt. % of $B_2O_3$ (Ca/P=1.67) and ground in a mortar. This glass batch was melted using a platinum crucible at 1,250° C. for 3 hours and cast in a mold to give a rectangular block measuring $10 \times 10 \times 20$ mm$^3$. This glass block was heat-treated at 800° C. for 50 hours and subjected to X-ray diffraction analysis. The diffraction pattern showed that as in Example 1, the peak intensity of apatite was greater than those of tricalcium phosphate and aluminum phosphate.

EXAMPLE 4

$CaCO_3$, $H_3PO_4$, $Al_2O_3$ and $B_2O_3$ were taken to give a glass composition of 23.2 wt. % of CaO, 19.6 wt. % of $P_2O_5$ 31.4 wt. % of $Al_2O_3$ and 25.8 wt. % of $B_2O_3$ (Ca/P=1.5) and ground in a mortar. This glass batch was melted in a platinum crucible at 1,280° C. for 3 hours and cast in a mold to give a rectangular block measuring $10 \times 10'20$ mm$^3$. This glass block was heat-treated at 820° C. for 50 hours and subjected to X-ray diffraction analysis. As a result, three kinds of crystals precipitated with apatite crystals showing the greatest peak intensity just as in Example 1.

EXAMPLE 5

$CaCO_3$, $H_3PO_4$, $Al(OH)_3$, $B_2O_3$ and $SiO_2$ were taken to give a glass composition of 24.2 wt. % of CaO, 18.3 wt. % of $P_2O_5$, 31.9 wt. % of $Al_2O_3$, 21.9 wt. % of $B_2O_3$ and 3.7 wt. % of $SiO_2$ (Ca/P=1.67) and ground in a mortar. The resulting glass batch was melted in a platinum crucible at 1,320° C. for 3 hours and the melt was cast in a mold to give a rectangular block measuring $10\times10\times20$ mm$^3$. This glass block was heat-treated at 810° C. for 50 hours, whereupon crystals of apatite, tricalcium phosphate and aluminum phosphate precipitated. X-ray diffraction analysis showed that the peak intensity of apatite crystals was the greatest of all precipitated crystals.

EXAMPLE 6

$CaCO_3$, $NH_4H_2PO_4$, $Al_2O_3$, $B_2O_3$ and $Li_2CO_3$ were taken to give a glass composition of 21.3 wt. % of CaO, 16.1 wt. % of $P_2O_5$, 37.7 wt. % of $Al_2O_3$, 24.2 wt. % of $B_2O_3$ and 0.7 wt. % of $Li_2O$ (Ca/P=1.67) and ground in a mortar to give a glass batch. The glass batch was melted in a platinum crucible at 1,280° C. for 3 hours and cast in a mold to prepare a rectangular block measuring $10\times10\times20$ mm$^3$. This glass block was heat-treated at 770° C. for 30 hours, whereupon a glass ceramic including precipitates of apatite, tricalcium phosphate and aluminum phosphate crystals was obtained. X-ray diffraction analysis showed that the peak intensity of apatite was the greatest of all the crystals.

EXAMPLE 7

$CaCO_3$, $H_3PO_4$, $Al_2O_3$, $B_2O_3$ and $TiO_2$ were taken to give a glass composition of 20.9 wt. % of CaO, 15.8 wt. % of $P_2O_5$, 37.1 wt. % of $Al_2O_3$, 21.3 wt. % of $B_2O_3$ and 4.9 wt. % of $TiO_2$ (ca/P=1.67) and ground in a mortar to give a glass batch. This glass batch was melted in a platinum crucible at 1,320° C. for 3 hours and cast to give a rectangular block measuring $10\times10\times20$ mm$^3$. The glass block was heat-treated at 810° C. for 40 hours to prepare a glass ceramic in which apatite, tricalcium phosphate and aluminum phosphate had been precipitated. The X-ray diffraction pattern of this glass ceramic showed that the peak intensity of apatite was the greatest.

EXAMPLE 8

$CaCO_3$, $H_3PO_4$, $Al_2O_3$ and $B_2O_3$ were taken to give a glass composition of 25.1 wt. % of CaO, 24.7 wt. % of $P_2O_5$, 29.8 wt. % of $Al_2O_3$, 20.4 wt. % of $B_2O_3$ (Ca/P=1.67) and ground in a mortar to give a glass batch. This glass batch was melted in a platinum crucible at 1,300° C. for 3 hours and cast in a mold to prepare a crown-shaped block. This glass block was heat-treated at 800° C. for 50 hours, whereby apatite, tricalcium phosphate and aluminum phosphate crystals were precipitated as in Example 1. The X-ray diffraction pattern of this crown-shaped cast product showed that the apatite crystals had the greatest peak intensity.

EXAMPLE 9

$CaCO_3$, $H_3PO_4$, $Al_2O_3$ and $B_2O_3$ were taken to give a glass composition of 21.5 wt. % of CaO, 16.2 wt. % of $P_2O_5$, 31.8 wt. % of $Al_2O_3$ and 30.5 wt. % of $B_2O_3$ and ground in a mortar to give a glass batch. This glass batch was melted in a platinum crucible at 1,250° C. for 3 hours to give a rectangular block measuring $10\times10\times20$ mm$^3$. This glass block was crystallized at 800° C. for 50 hours to give a glass ceramic in which apatite, tricalcium phosphate and aluminum phosphate crystals had been precipitated. The X-ray diffraction pattern of this product showed that the peak intensity of apatite crystals was the greatest.

EXAMPLE 10

$CaCO_3$, $H_3PO_4$, $Al_2O_3$ and $B_2O_3$ were taken to give a glass composition of 25.1 wt. % of CaO, 24.7 wt. % of $P_2O_5$, 29.8 wt. % of $Al_2O_3$ and 20.4 wt. % of $B_2O_3$ (Ca/P=1.67) and ground in a mortar. The resulting glass batch was melted in a platinum crucible at 1,300° C. for 3 hours and cast in a mold to give a rectangular glass block measuring $10\times10\times20$ mm$^3$. This glass block was composed exclusively of glass phase. This glass block was heat-treated at 750° C. for 10 hours to give a glass ceramic containing apatite crystals. The heat-treated block was cut with a diamond disk and the four sides were polished with alumina to prepare ten testpieces each measuring $3\times4\times30$ mm$^3$. The determination of strength was carried out by the 3-point bending test using a span of 20 mm and a crosshead speed of 0.5 mm/min. The radii of the lower fulculum and crosshead were as specified in JIS R-1601. The mean value of 3-point bending strength of 10 testpieces was 1,800 Kg/cm$^2$.

COMPARATIVE EXAMPLE 1

$CaCO_3$, $H_3PO_4$, $Al_2O_3$ and $B_2O_3$ were taken to give a glass composition of 27.8 wt. % of CaO, 20.9 wt. % of $P_2O_5$, 19.7 wt. % of $Al_2O_3$ and 31.6 wt. % of $B_2O_3$ (Ca/P=1.67) and ground in a mortar to give a glass batch. This glass batch was melted in a platinum crucible at 1,300° C. for 3 hours and solidified to give a rectangular block measuring $10\times10\times20$ mm$^3$. By this procedure, there could not be obtained a cast product exclusively composed of glass phase.

COMPARATIVE EXAMPLE 2

$CaCO_3$, $H_3PO_4$, $Al_2O_3$ and $B_2O_3$ were taken to give a glass composition of 25.7 wt. % of CaO, 19.3 wt. % of $P_2O_5$, 42.5 wt. % of $Al_2O_3$ and 12.5 wt. % of $B_2O_3$ (Ca/P=1.67) and ground in a mortar to give a glass batch. This glass batch was melted in a platinum crucible but it could not be sufficiently melted.

COMPARATIVE EXAMPLE 3

$CaCO_3$, $H_3PO_4$, $Al_2O_3$ and $B_2O_3$ were taken to give a glass composition of 16.2 wt. % of CaO, 12.3 wt. % of $P_2O_5$, 31.0 wt. % of $Al_2O_3$ and 39.5 wt. % of $B_2O_3$ (Ca/P=1.67) and ground in a mortar to give a glass batch. This glass batch was melted in a platinum crucible at 1,250° C. for 3 hours and cast to give a rectangular block measuring $10\times10\times20$ mm$^3$. This glass block was heat-treated but there was no evidence of precipitation of crystals in any of X-ray diffraction analysis, differential thermal analysis and macroscopic observation.

COMPARATIVE EXAMPLE 4

$CaCO_3$, $H_3PO_4$, $Al_2O_3$ and $B_2O_3$ were taken to give a glass composition of 23.7 wt. % of CaO, 24.8 wt. % of $P_2O_5$, 30.5 wt. % of $Al_2O_3$ and 21.0 wt. % of $B_2O_3$ (Ca/P=1.2) and ground in a mortar to give a glass batch. This glass batch was melted in a platinum crucible at 1,300° C. for 3 hours and cast to give a rectangular block measuring $10\times10\times20$ mm$^3$. When this glass block was crystallized at 800° C., the resulting glass ceramic included non-apatite phosphate crystals as predominant crystals.

COMPARATIVE EXAMPLE 5

$CaCO_3$, $H_3PO_4$, $Al_2O_3$ and $B_2O_3$ were taken to give a glass composition of 28.2 wt. % of CaO, 17.7 wt. % of $P_2O_5$, 32.1 wt. % of $Al_2O_3$ and 22.0 wt. % of $B_2O_3$ (Ca/P=2.0) and ground in a mortar to give a glass batch. This glass batch was melted in a platinum crucible at 1,450° C. for 10 hours and cast in a mold to give a rectangular block measuring 10×10×20 mm³. However, there could not be obtained a cast product composed exclusively of glass phase.

COMPARATIVE EXAMPLE 6

$CaCO_3$, $H_3PO_4$, $Al_2O_3$, $B_2O_3$ and $SiO_2$ were taken to give a glass composition of 21.2 wt. % of CaO, 15.8 wt. % of $P_2O_5$, 31.1 wt. % of $Al_2O_3$, 21.5 wt. % of $B_2O_3$ and 10.5 wt. % of $SiO_2$(Ca/P=1.67) and melted at 1,350° C. for 5 hours. The melt was cast to give a rectangular block measuring 10×10×20 mm³. However, there could not be obtained a cast product composed exclusively of glass phase.

COMPARATIVE EXAMPLE 7

$CaCO_3$, $H_3PO_4$, $Al(OH)_3$ and $B_2O_3$ were taken to give a glass composition of 29.6 wt. % of CaO, 25.0 wt. % of $P_2O_5$, 22.7 wt. % of $Al_2O_3$, 9.1 wt. % of $B_2O_3$ and 13.6 wt. % of $SiO_2$(Ca/P=1.50) and ground in a mortar. The resulting glass batch was melted in a platinum crucible at 1,450° C. and cast in a mold to give a glass block measuring 10×10×30 mm³. When the crystallization temperature of this glass was analyzed by differential thermal analysis, the exothermic peak was found at about 1,000° C. Powder X-ray diffraction analysis revealed that the precipitated crystals were tricalcium phosphate crystals with a low Ca/P ratio. As in Example 10, the above glass ceramic was cut and polished and its 3-point bending strength was determined at a crosshead speed of 0.5 mm/min. and a span of 20 mm. The mean strength value of 10 testpieces was 1,200 Kg/cm².

COMPARATIVE EXAMPLE 8

$CaCO_3$, $H_3PO_4$, $Al_2O_3$ and $B_2O_3$ were taken to give a glass composition of 31.85 wt. % of CaO, 24.15 wt. % of $P_2O_5$, 20.0 wt. % of $Al_2O_3$ and 24.0 wt. % of $B_2O_3$ (Ca/P=1.67) and ground in a mortar. This glass batch was melted in a platinum crucible at 1,300° C. for 3 hours and cast in a mold to give a glass block measuring 10×10×30 mm³. This block contained no crystal phases. However, after crystallization at 750° C. for 10 hours, the crystallized region and the glassy region were separately observed in the block with the naked eye and the mean value of 3-point bending strength of 10 testpieces was only about 500 Kg/cm².

Owing to the presence of apatite crystals as a dominant crystal phase in the glass matrix, the glass ceramic of the present invention has excellent biocompatibility. Since it can be fused at a low temperature, it is now made easily possible to provide a glass ceramic having virtually any desired shape. The glass ceramic of this invention not only has mechanical properties required of biological materials but, because of the presence of apatite crystals as dominant crystals therein, offers the advantage that it is less liable to release glass components in vivo than those glasses containing other calcium phosphate crystals as dominant crystals. Therefore, the glass ceramic according to this invention is of value for use as various biological materials and particularly as artificial dental prostheses.

What is claimed is:

1. A glass ceramic comprising at least 90 weight percent of a glass composed of

CaO : 17-28 weight percent $P_2O_5$ : 13-26 weight percent $Al_2O_3$ : 25-38 weight percent $B_2O_3$ : 20-37 weight percent (all based on the weight of the glass ceramic), with the atomic ratio of calcium to phosphorus within the range of 1.30 to 1.75, and apatite crystals dispersed as dominant crystals in said glass.

2. The glass ceramic of claim 1 wherein nucleating agent is contained in proportion less than 10 weight percent based on the total weight of the glass ceramic.

* * * * *

UNITED STATES PATENT AND TRADEMARK OFFICE
CERTIFICATE OF CORRECTION

PATENT NO. : 4,829,026

DATED : May 9, 1989

INVENTOR(S) : Katsuaki TAKAHASHI, et al.

It is certified that error appears in the above-identified patent and that said Letters Patent is hereby corrected as shown below:

On cover page of the patent, please insert --[30] Foreign Application Priority Data May 11, 1987 [JP] Japan ....... 62-115434--; Column 3, line 44, where "m elted" should read --melted--; Column 4, line 31, where "by" should read --By--; Column 4, line 55, where 10X10'20" should real --10X10X20--; Column 5, line 67, where "$Al_{2⁄}O_3$" should read --$Al_2O_3$--.

Signed and Sealed this

Sixth Day of March, 1990

Attest:

JEFFREY M. SAMUELS

*Attesting Officer*   *Acting Commissioner of Patents and Trademarks*